United States Patent [19]
Thomas, III et al.

[11] Patent Number: 5,226,847
[45] Date of Patent: Jul. 13, 1993

[54] APPARATUS AND METHOD FOR ACQUIRING IMAGING SIGNALS WITH REDUCED NUMBER OF INTERCONNECT WIRES

[75] Inventors: Lewis J. Thomas, III, Schenectady; Ralph A. Hewes, Burnt Hills, both of N.Y.

[73] Assignee: General Electric Company, Schenectady, N.Y.

[21] Appl. No.: 830,020

[22] Filed: Jan. 31, 1992

Related U.S. Application Data

[63] Continuation-in-part of Ser. No. 451,060, Dec. 15, 1989, abandoned.

[51] Int. Cl.$^5$ ............................................. A61B 8/00
[52] U.S. Cl. ................................ 128/662.06; 73/623
[58] Field of Search ............ 128/662.6, 661.01, 660.07; 73/623, 625-626

[56] References Cited

U.S. PATENT DOCUMENTS

| | | | |
|---|---|---|---|
| 4,135,139 | 1/1979 | Buchner | 128/661.01 |
| 4,344,159 | 8/1982 | Ballinger | 367/87 |
| 4,470,308 | 9/1984 | Hayakawa et al. | 73/642 |
| 4,534,221 | 8/1985 | Fife et al. | 73/626 |
| 4,911,170 | 3/1990 | Thomas, III et al. | 128/662.06 |
| 4,917,097 | 4/1990 | Proudian et al. | 128/662.06 |

FOREIGN PATENT DOCUMENTS

| | | | |
|---|---|---|---|
| 2208138 | 3/1989 | United Kingdom | 128/662.06 |
| 8904142 | 5/1989 | United Kingdom | |

*Primary Examiner*—Francis Jaworski
*Attorney, Agent, or Firm*—Marvin Snyder

[57] ABSTRACT

Apparatus for echo mode imaging of a blood vessel is disclosed having a plurality of transducers that transmit a substantially unfocused omni-directional signal in at least one plane towards the vessel. The reflected signal is received and transmitted in time multiplexed form to an Analog-to-Digital converter. Thus the required number of interconnecting wires is reduced. A method for imaging a blood vessel comprises transmitting an unfocused signal in a substantially omni-directional manner in at least one plane, receiving reflections from the vessel, and transmitting the received signals in time multiplexed form for imaging.

27 Claims, 2 Drawing Sheets

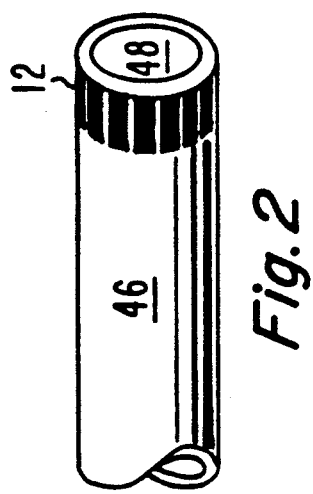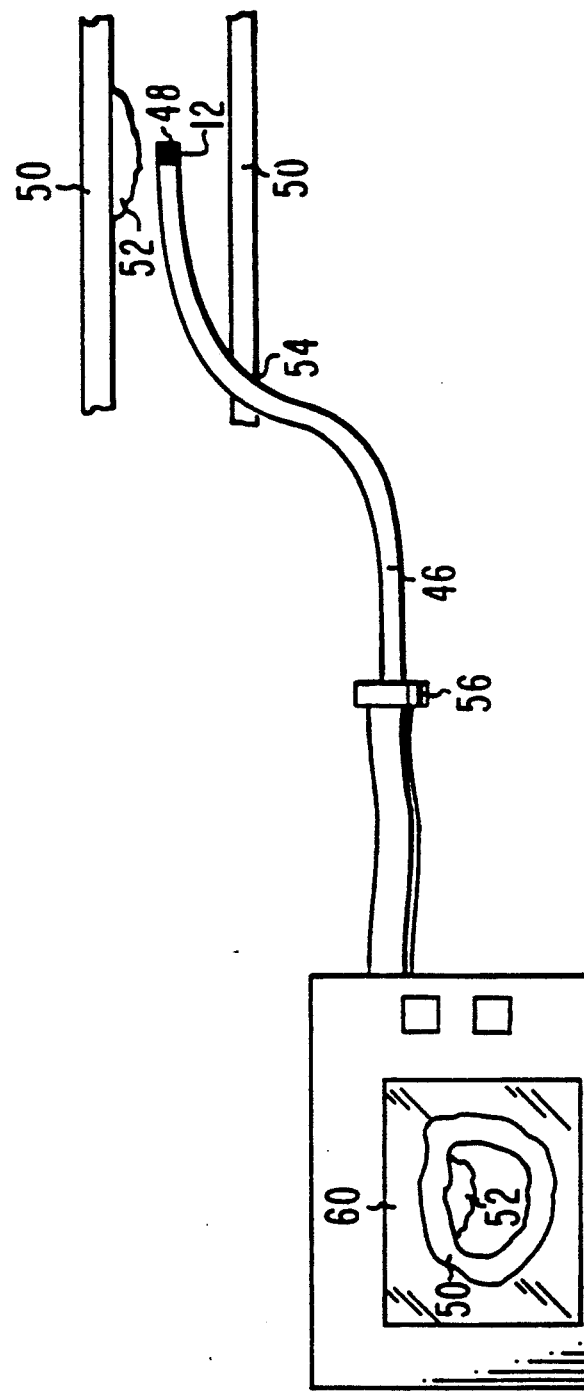

APPARATUS AND METHOD FOR ACQUIRING IMAGING SIGNALS WITH REDUCED NUMBER OF INTERCONNECT WIRES

CROSS REFERENCE TO RELATED APPLICATION

This is a continuation-in-part of patent application Ser. No. 07/451,060 filed Dec. 15, 1989, and now abandoned.

Reference is made to U.S. Pat. No. 4,911,170, by Lewis J. Thomas et al, entitled "High Frequency Focused Ultrasonic Transducer for Invasive Tissue Characterization," which is assigned to the same assignee as the present invention.

BACKGROUND OF THE INVENTION

The present invention relates to imaging apparatus and method, and more particularly, to an ultrasonic medical imaging catheter.

Conventional medical ultrasonic transducer technology typically has a plurality of pulse driven piezoelectric transducer elements. Phasing techniques are used to drive the transducers to synthesize a one or two dimensional phased array to obtain a high resolution image, such as known in the radar art. This requires that each element in the array be individually driven (pulsed) and have a receive circuit since signals both to and from the transducer elements must be delayed in order to focus the ultrasonic signals. Thus, if there are n number of transducers, n number of interconnect wires and a ground return wire, or a total of n+1 interconnect wires, are required. If it is desired to place the transducers on the tip of a catheter for intralumenal (from the inside) imaging, the number of wires which may be brought back up the catheter is limited by the wire diameter and catheter size. Since a typical minimum number of catheter transducers is about 256, 257 wires would be required for adequate beam forming and thus image resolution. It is desired to reduce this impractically large number to a minimum by implementing an appropriate multiplexing feature.

In U.K. patent no. 8,904,142 issued May 18, 1989 by Kitney et al, there is illustrated a crosswiring arrangement describing a hardwired multiplexing feature. However, the hardwired apparatus appears to multiplex signals on both transmit and receive and would be too lossy to operate as a useful multiplexer for low amplitude signals obtained from low capacitance components. It is an object of the instant invention to overcome these limitations.

In U.S. Pat. No. 4,917,097 issued Apr. 17, 1990 by Proudian et al, a typical synthetic aperture focusing technique is described for transmitting and receiving over one element at a time providing a multiplexing feature which is lossy for low capacitance components. It is therefore an object of the instant invention to overcome this limitation.

In U.S. Pat. No. 4,470,308 issued Sep. 11, 1984 by Hayakawa et al, transducers are directly coupled to a multiplexing means wherein multiplexing is controlled by counters in order to determine variable time delays and compensate for phasing between signals. It is another object of the instant invention to utilize phasing itself as a mechanism to steer and focus the beam.

In U.S. Pat. No. 4,344,159 issued Aug. 10, 1982 by Ballinger and U.S. Pat. No. 4,534,221 issued Aug. 13, 1985 by Fife et al signal isolation is accomplished using isolation diodes. Cross diodes are typically used to isolate low amplitude componenet signals. Ballinger utilizes similar signal isolation then compensates for signal phasing differences. It is yet another object of the instant invention to isolate signals having low amplitude in order to specifically isolate phasing differences; thereby employing phasing itself to steer and focus the beam.

In U.S. Pat. No. 4,911,170 issued Mar. 27, 1990 by Thomas, III et al and assigned to the same assignee as the present invention, a high frequency ultrasonic transducer for characterizing interlumenal arterial features is described. It is still another object of the instant invention to accomodate such high frequency imaging transducers with an improved interlumenal catheter signal acquisition system.

It is therefore an object of the present invention to provide apparatus and method to achieve a sufficiently high resolution image while obtaining a reduction in the number of connecting wires especially when transducers are at a catheter tip.

SUMMARY OF THE INVENTION

In brief, this and other objects are achieved by apparatus for acquiring signals for intralumenal imaging comprising: means for simultaneously transmitting a plurality of omni-directional ultrasound signals from an enclosed transceiver array in order to provide successive simultaneous transmissions which impinge upon a reflective lumenal surface; and a locally disposed time division multiplexing means coupled to the transceiver array which receives a corresponding plurality of reflected signals for imaging; wherein local multiplexing on receive reduces the number of required interconnecting wires to a minimum of two.

A method in accordance with the invention for imaging features of a lumenal surface comprises successively transmitting from an intralumenal site a plurality of simultaneous unfocussed ultrasound signals being substantially omni-directional in order to reflect from the lumenal surface; receiving a corresponding plurality of reflected signals therefrom via said transceiver array; and sequentially time division multiplexing said received signals in a select manner at the intralumenal site.

BRIEF DESCRIPTION OF THE DRAWING

FIG. 2 is a close up isometric view of an end of a catheter having transducers disposed thereon; and FIG. 3 is a view of the catheter inserted into a blood vessel and coupled to a display.

DETAILED DESCRIPTION

Figure 1:
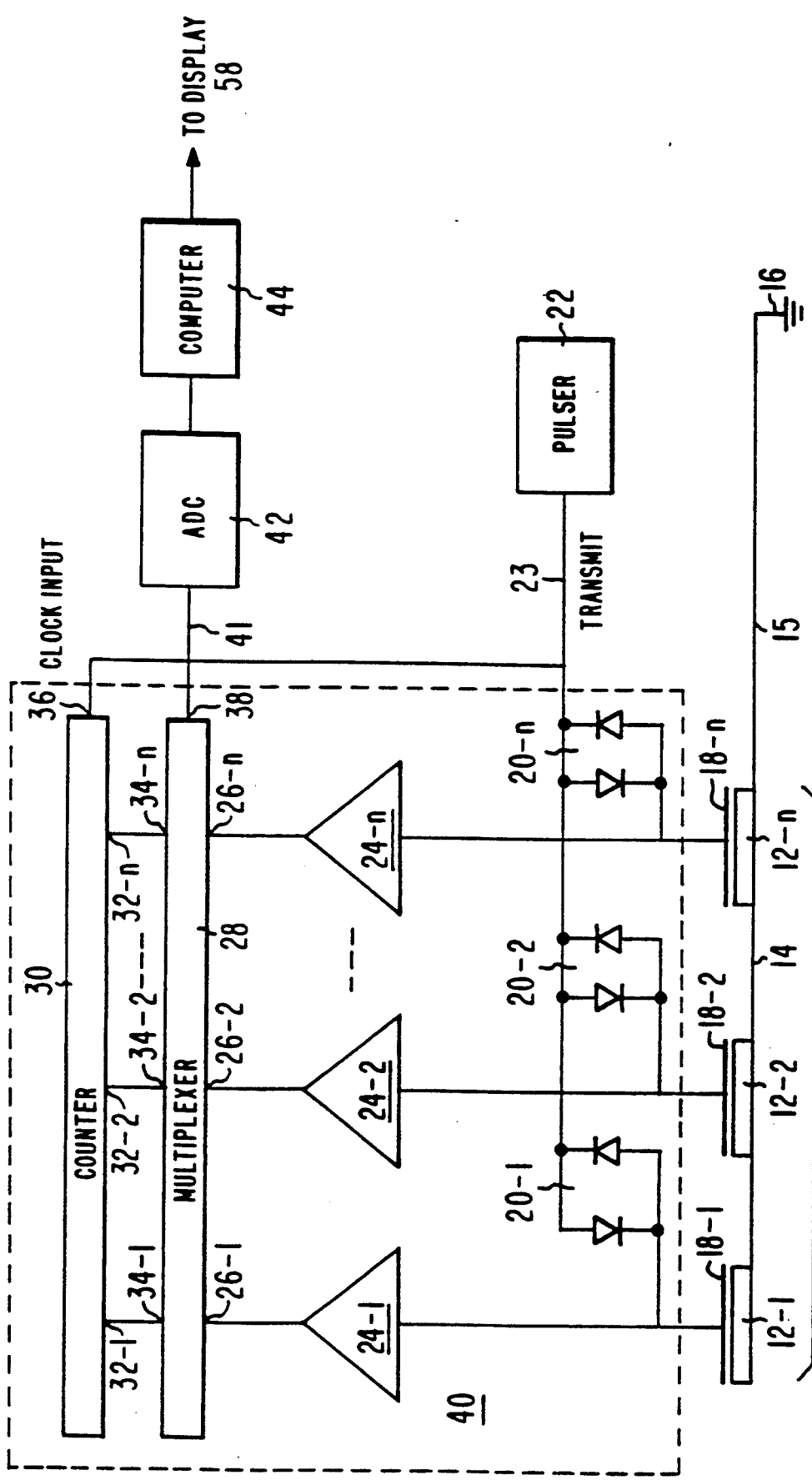
FIG. 1 is a partly block and partly schematic diagram of the circuit of the invention.

FIG. 1 shows a transducer array 10 comprising a plurality of transducers 12-1, 12-2, . . . 12-n, which are typically located at a catheter (described below). Transducers 12 typically comprise a piezoelectric, e.g., barium titanate, polyvinylidine difluoride, etc., or can comprise a capacitive transducer, and are interconnected by a common electrode 14 that engages one side thereof. Electrode 14 is grounded by means of grounding first interconnect wire 15 at a location 16, typically a display (described below), that is external to the catheter. The other side of transducers 12 respectively have electrodes 18-1, 18-2, . . . 18-n that are respectively coupled to antiparallel coupled diode pairs 20-1, 20-2, . . . 20-n.

In turn, diode pairs 20 are coupled to a pulser 22 by means of a transmitting second interconnect wire 23. Pulser 22 typically produces approximate half cycle pulses of RF with a center frequency between about 0.5 to 100 MHz, preferably about 40 MHz. Other pulse waveforms can be used. If an approximate half cycle pulse of a 40 MHz center frequency is used, the result is a very broadband signal, i.e., between about 0 to 80 MHz, generated by pulser 22. However, typically transducers 12 have a bandwidth between about 20 to 60 MHz, and thus only these frequencies will be emitted. Transducers 12, diode pairs 20 and pulser 22 comprise a transmitting means.

Electrodes 18 are also respectively coupled to the inputs of amplifiers 24-1, 24-2, ... 24-n, the outputs of which are respectively coupled to signal inputs 26-1, 26-2, ... 26-n of a time division multiplexer (TDM) 28. A counter 30 has outputs 32-1, 32-2, ... 32-n respectively coupled to control inputs 34-1, 34-2, ... 34-n of TDM 28. Counter 30 also has a clock input 36 coupled to pulser 22. Diode pairs 20, amplifiers 24, TDM 28, and counter 30 are preferably formed in a single integrated circuit 40, which is typically located in the catheter. An output 38 of TDM 28 is coupled by way of a receiving third interconnect wire 41 to analog-to-digital converter (ADC) 42. In turn, the output of ADC 42 is coupled to a computer 44. The output of computer 44 is applied to a display 58 (described below). Transducers 12, amplifiers 24, multiplexer 28, counter 30, ADC 42, and computer 44 comprise a receiving means. Thus transducers 12 are part of both the transmitting and receiving means. There is a fourth interconnect wire (not shown) present that supplies power to circuit 40. All four interconnect wires run through the length of the catheter.

FIG. 2 shows a catheter 46 having a sealed end 48. Transducers 12 are outwardly facing and peripherally disposed near end 48 at substantially equal angles, preferably with a circumferential center-to-center spacing of about one half of the center frequency, e.g., 40 MHz, sonic wavelength in water. This wavelength in water is about the same as the wavelength in blood. As a non-limiting example, consider catheter 46 having an outside diameter of 2 mm and pulser 22 having a center frequency of 40 MHz. Then transducers 12 would be in number about 335. Usually, the number of transducers 12 selected to be a power of two for easy digital binary processing so that either 256 or 512 would be chosen as the number of transducers 12. Other geometries for the disposition of transducers 12 as well as other numbers of transducers can be used. If desired, a slight increase in image resolution can be obtained if the spacing is reduced to one half wavelength at the highest emitted frequency, e.g., 60 MHz.

FIG. 3 shows a cylindrical shaped blood vessel 50, e.g., vein, artery, capillary, etc., having a plaque deposit 52 on the interior wall thereof. The end 48 of catheter 46 is inserted into vessel 50 by way of an incision 54. The other end of catheter 46 has a coupling 56 thereon, which provides the interconnects to a display 58, which in turn provides a displayed image 60. Display 58 typically houses pulser 22, ADC 42, computer 44, a power supply (not shown) for circuit 40, a scan converter (not shown) as well as conventional display circuits.

In operation, the first step is transmit, and therefore pulser 22 provides a pulse of RF. Since the output voltage of pulser 22 is usually quite high, e.g., about 100–300 volts, the transmit pulse is conducted by all of the diode pairs 20 and therefore simultaneously excites all of the transducers 12 in parallel manner. This simultaneous pulsing of all transducers improves the overall signal to noise ratio of low amplitude signals obtained from low capacitance transducer components. The parallel collective electrical capacitance of tranducers 12 inherently improves the overall signal obtained therefrom. Therefore, the transmitted field represents an improved omni-directional, unfocussed surface generated longitudinal wave having a shape determined by the disposition of transducers 12 in order to propagate toward a facing surface enclosing the array. For example, if the elements are arrayed in a circle facing outward, as shown in FIG. 2, then the resulting acoustic field will be a cylindrically shaped wave. Such a wave is substantially non-directional in at least the plane perpendicular to the longitudinal axis of catheter 46 and through the middle of transducers 12.

The transmitted wave is then reflected from plaque 52 and the interior walls of vessel 50. The reflected wave is then incident upon transducers 12, which generate signals.

During receive, which occurs between transmit pulses, the voltages of the signals generated by the transducers 12 are lower than the forward voltage drop, i.e., about 0.7 volts, of the diode pairs 20. Thus pairs 20 are nonconductive, and therefore the signals from transducers 12 are respectively applied only to amplifiers 24. The multiplexer 28 selects one of the transducers 12 and applies its amplified signal to interconnect line 41. On each transmit pulse the counter 30 increments by one, thereby changing which one of the amplified signals that multiplexer 28 selects to connect to line 41. The analog signal on line 41 is converted to a digital signal by ADC 42 and applied to computer 55. After a number of transmit pulses equal to the number of elements in the array, enough data for one complete image has been collected in computer 42. Then the receive operation is repeated starting with that particular one of transducers 12 that was initially read out of multiplexer 28.

Once data for a complete image signal has been collected, the image signal is generated in computer 42 using conventional phased array received focussing techniques, i.e., time delaying by the propagation time between a particular transducer and the focussed point. Programs for performing such an operation are known in the radar and ultrasonic imaging arts. Since the present invention only requires focussing during the receive operation, the program for the present invention would comprise essentially one half of said known prior art programs. The digital image signal from computer 44 is applied to a conventional scan converter (not shown), which converts the digital signal to an analog signal and formats it into a standard format, e.g., NTSC. This signal is then applied to the remainder of the circuits in display 58., which are conventional. The images would be formed in real-time, meaning that the image would be displayed at the maximum frame rate the data collected allows; however, the fact that many transmit/receive cycles must occur before the image is formed means that the displayed image will lag behind the data collection, probably by one frame, or about 1/30 of a second if display 56 is of the NTSC type.

It will be appreciated that the present invention drastically reduces the number of required interconnect wires although some sacrifice in the picture quality results since there is no focussing during the transmit operation. This has been found to be acceptable in medical imaging. It will be further appreciated that many other embodiments are within the spirit and scope of the invention. For example, for non-medical uses, electromagnetic instead of sound waves would be used. In general, the present invention is useful in any situation where the data channels must be limited in number and some sacrifice in picture quality is permissible.

What is claimed is:

1. Apparatus for acquiring a select plurality of signals for imaging enclosing surface features of an object, said apparatus comprising:

transducer array means adapted to be positioned internal to the enclosing surface; said array means being adapted for simultaneously transmitting a plurality of signals to said enclosing surface, said signals being transmitted in an omni-directional manner as an unfocussed longitudinal wave emanating from said array means toward said enclosing surface in order to reflect therefrom;

time division multiplexing means disposed proximate to said transducer array means and coupled thereto for receiving from said transducers of said array means a corresponding plurality of time delayed signals reflected from said enclosing surface for imaging thereof;

at least one transmit lead for coupling said transducer array means to an external driving means; and at least one receive lead for coupling said time division multiplexing means to external image processing means.

2. The apparatus of claim 1 wherein said object is substantially cylindrical in shape.

3. The apparatus of claim 2 wherein enclosing surface features of said object comprise intralumenal plaque of a blood vessel.

4. The apparatus of claim 1 wherein said transducer array means comprises a plurality of piezoelectric transducers disposed in an array.

5. The apparatus of claim 4 further comprising a catheter, said transducers being disposed with substantially uniform peripheral spacing on the outward facing surface of said catheter.

6. The apparatus of claim 5 wherein said transducers are circumferentially spaced about one half a wavelength apart wherein said wavelength is a sonic wavelength in water determined for a center frequency of said transmitted wave.

7. The apparatus of claim 5 wherein said external driving means comprises a pulser disposed outside said catheter and coupled in parallel to said transducer array means.

8. The apparatus of claim 7 wherein a plurality of antiparallel connected diode pairs are disposed in said catheter said pairs being respectively coupled to said transducers and to said pulser.

9. The apparatus of claim 8 wherein said wave comprises a pulsed ultrasonic wave.

10. The apparatus of claim 9 wherein said wave has center frequency between about 0.5 MHz to 100 MHz.

11. The apparatus of claim 10 wherein said wave has center frequency of about 40 MHz.

12. The apparatus of claim 7 further comprising a counter coupled to said multiplexing means.

13. The apparatus of claim 12 wherein said multiplexing means and said counter are disposed on the inside of said catheter.

14. The apparatus of claim 13 wherein said apparatus further comprises an analog-to-digital converter coupled to said multiplexing means and a computer coupled to said converter; wherein said pulser is coupled to said transducers, and said counter.

15. The apparatus as claimed in claim 14 further comprising a display means disposed outside said catheter wherein said image processing means includes said converter, said computer, and said display means.

16. The apparatus of claim 13 further comprising an integrated circuit comprising said multiplexing means and said counter, said integrated circuit further comprising a plurality of antiparallel coupled diode pairs, said pairs being respectively coupled to said transducer and to said pulser.

17. The apparatus of claim 15 wherein said integrated circuit further comprises a plurality of amplifiers respectively coupled between said transducers and said counter.

18. The apparatus of claim 5 wherein said catheter is a cylindrical catheter, and said transducers are circumferentially spaced about said catheter in order to transmit omni-directionally in at least a plane through said transducers.

19. Apparatus for acquiring a plurality of signals for imaging intralumenal surface features of a blood vessel, said apparatus comprising:

a catheter having an end, said catheter capable of being disposed in said blood vessel;

a plurality of ultrasonic transducers peripherally disposed on said catheter proximate to said end for simultaneously transmitting a plurality of transduced ultrasound signals and receiving a correspondingly transduced plurality of reflected ultrasonic signals;

a plurality of antiparallel connected diode pairs disposed in said catheter and respectively coupled to said transducers;

a time division multiplexing means disposed in said catheter and coupled to said transducers for selectively multiplexing said received signals only; and a counter disposed in said catheter and coupled to said multiplexing means.

20. The apparatus of claim 19 further comprising a plurality of amplifiers respectively coupled between said transducers and said counter.

21. The apparatus of claim 19 further comprising a pulser coupled to said pairs and said counter.

22. The apparatus of claim 19 further comprising an analog-to-digital converter coupled between said multiplexing means and a computer.

23. A method for acquiring a select plurality of signals for imaging enclosing surface features of an object, said method comprising:

simultaneously transmitting a plurality of signals from a plurality of transducers disposed at an enclosed site to provide an unfocused longitudinal wave emanating in an omni-directional manner for successive transmission toward said enclosing surface of said object;

receiving a corresponding plurality of time delayed signals reflected from said enclosing surface at said plurality of transducers; and selectively time division multiplexing said sequentially received signals at said enclosed site for imaging thereof.

24. The method of claim 23 wherein said transmitting step comprises transmitting an ultrasonic signal.

25. A method of claim 23 wherein said transmitting and receiving steps comprise transducing from a catheter.

26. The method of claim 23 wherein said transmitting step comprises pulsing.

27. The method of claim 23 further comprising analog-to-digital converting said signals after multiplexing.

* * * * *